US009861442B2

(12) United States Patent
Tankovich et al.

(10) Patent No.: US 9,861,442 B2
(45) Date of Patent: Jan. 9, 2018

(54) LASER FILLER (71) Applicants: Nikolai Tankovich, San Diego, CA (US); Alexei Lukashev, San Diego, CA (US)

(72) Inventors: Nikolai Tankovich, San Diego, CA (US); Alexei Lukashev, San Diego, CA (US)

(*) Notice: Subject to any disclaimer, the term of this patent is extended or adjusted under 35 U.S.C. 154(b) by 18 days.

(21) Appl. No.: 14/215,057

(22) Filed: Mar. 16, 2014

(65) Prior Publication Data
US 2015/0257828 A1 Sep. 17, 2015

(51) Int. Cl.
*A61B 18/20* (2006.01)
*A45D 26/00* (2006.01)
*A45D 34/04* (2006.01)
*A61M 35/00* (2006.01)
*A61B 18/18* (2006.01)
*A61B 17/00* (2006.01)
*A61B 18/00* (2006.01)
*A61N 5/06* (2006.01)
*A61N 5/067* (2006.01)

(52) U.S. Cl.
CPC ............ *A61B 18/203* (2013.01); *A45D 26/00* (2013.01); *A45D 34/04* (2013.01); *A45D 2026/009* (2013.01); *A61B 18/1815* (2013.01); *A61B 2017/00756* (2013.01); *A61B 2018/00017* (2013.01); *A61B 2018/0047* (2013.01); *A61B 2018/00476* (2013.01); *A61B 2018/202* (2013.01); *A61M 35/00* (2013.01); *A61N 2005/067* (2013.01); *A61N 2005/0644* (2013.01); *A61N 2005/0659* (2013.01)

(58) Field of Classification Search
CPC ... A61B 18/20; A61B 2018/20; A61C 1/0046; A61N 5/06
See application file for complete search history.

(56) References Cited

U.S. PATENT DOCUMENTS

| | | | | |
|---|---|---|---|---|
| 5,415,652 A * | 5/1995 | Mueller | ............... | A61C 1/0046 604/27 |
| 5,616,141 A * | 4/1997 | Cipolla | ............... | A61C 1/0046 433/141 |
| 7,306,459 B1 * | 12/2007 | Williams | ................ | A61C 5/00 433/217.1 |
| 2002/0183727 A1 * | 12/2002 | Daikuzono | ............ | A61B 18/20 606/10 |
| 2003/0004499 A1 * | 1/2003 | McDaniel | ............ | A61B 18/203 606/3 |

(Continued)

FOREIGN PATENT DOCUMENTS

DE 4030734 A1 * 4/1991 ............. A61B 18/22

*Primary Examiner* — Lynsey Eiseman
(74) *Attorney, Agent, or Firm* — Law Office of Timothy M. Brown (57) ABSTRACT

The present invention provides a laser system and laser handpiece and process for skin treatment. The system includes components for producing a continuous or pulse laser beam, and components for delivering a substance to the damaged region of skin. The system is designed to control and utilize the laser beam for damaging small volume of skin tissue and using a disposable tip to deliver a substance which is applied simultaneously or with some delay producing a combination of laser action with the action of named substance at the same time.

19 Claims, 7 Drawing Sheets

(56) References Cited

U.S. PATENT DOCUMENTS

| | | | |
|---|---|---|---|
| 2005/0137584 A1* | 6/2005 | Lemchen | 606/1 |
| 2005/0222565 A1* | 10/2005 | Manstein | 606/41 |
| 2006/0074468 A1* | 4/2006 | Neev | A61B 18/203 607/90 |
| 2007/0225779 A1* | 9/2007 | Hantash | A61L 27/3804 607/89 |
| 2008/0255549 A1* | 10/2008 | Rose et al. | 606/15 |
| 2009/0130622 A1* | 5/2009 | Bollinger | A61C 1/0046 433/29 |
| 2011/0040235 A1* | 2/2011 | Castel | A61F 7/00 604/20 |
| 2011/0160712 A1* | 6/2011 | Tankovich | A61B 18/203 606/9 |
| 2014/0073996 A1* | 3/2014 | Jaguan | A61N 5/0618 601/15 |

\* cited by examiner

LASER FILLER

FIELD OF THE INVENTION

This invention relates to lasers, laser diodes, and solid state laser systems and in particular the use of those laser systems with a pre-filled medication/cosmeceuticals handpiece tip for skin treatment.

BACKGROUND OF THE INVENTION

Laser Diodes

Laser diodes are light sources where a direct current is applied to a semiconductor and electrical energy is transformed into laser light energy—the light is monochrome, coherent with high directionality. Laser diodes typically emit in a continuous wave mode or with relative long pulses (such as hundreds microseconds or more). Light power could be dozens of watts from one diode. Individual diodes can be assembled together to produce more power.

Solid State Lasers

Solid state lasers use solid crystals as an active medium and a flash lamp or laser diodes as a pump source. The laser pulse duration in solid state lasers could be from a dozen femtoseconds to several seconds or continuous wave. Laser energy could be from a fraction of millijoules up to dozens of Joules.

Wavelength Selection

Figure 7:
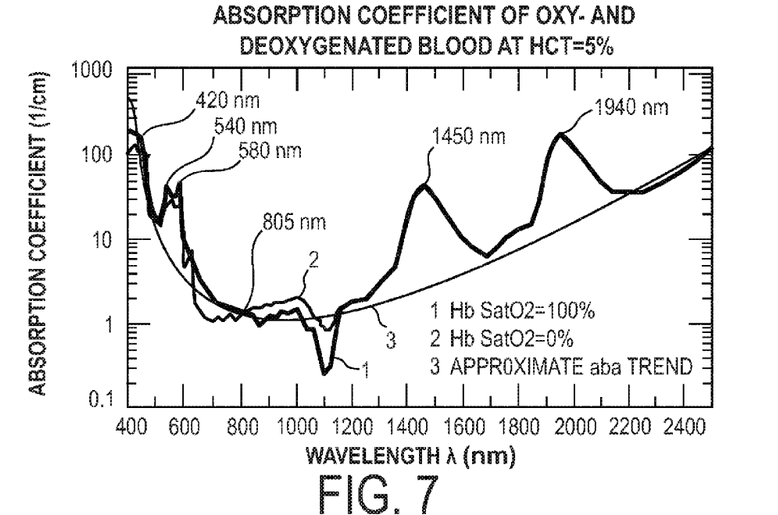
FIG. 7 is a graph showing absorption coefficients in blood.
Figure 8:
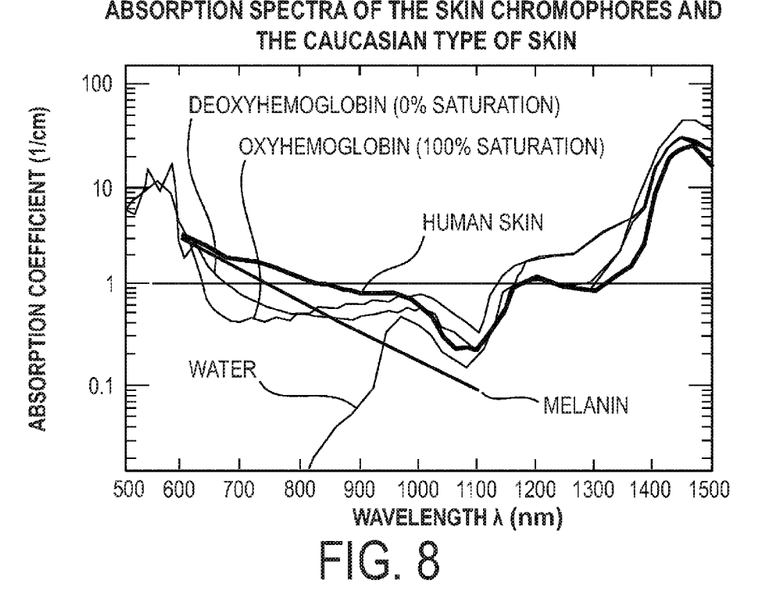
FIG. 8 is a graph showing absorption in skin.

Some wavelengths are very preferentially absorbed in a particular type of tissue when the tissue contains a particular chromophore that has a peak or relatively high absorption at the particular wavelength. After being absorbed in the tissue laser energy eventually transforms into thermal energy and results in rise of the temperature. Use of a laser beam matched to a peak or relatively high absorption in tissue to treat the tissue is referred to as "selective photothermolysis". Photothermolysis is a decomposition by temperature rise caused by light. Some wavelengths are absorbed relatively uniformly in tissue and when these wavelengths are used to treat the tissue it is referred to as "non-selective photothermolysis" or "homogeneous photothermolysis". Choice of wavelengths is important when these lasers are used in medicine and for surgery, tattoo removal, skin peeling and hair removal. Absorption in blood is lowest in a wavelength range between about 700 nm and about 1300 nm with peaks at 1450 nm and 1940 nm as shown in FIGS. 7 and 8 and absorption in Caucasian skin is lowest in a wavelength range between about 1050 nm and about 1150 and peaks in a wavelength of about 1480 as well as at 1930 nm as shown in FIG. 8.

Tissue Damage

In some medical laser applications, living tissue is intentionally modified or damaged with the laser energy. Modification of tissue depends on the volumetric laser energy deposition and pulse duration. In typical cases if the laser pulse is longer than several dozens of microseconds the typical result is temperature increase in the skin tissue caused by the energy of the laser beam being absorbed in the blood vessels, the blood in the vessels and the skin tissue. Temperature increase leads to tissue coagulation. In some cases tissue adjacent the target tissue can also be damaged. There exists, for normal skin tissue, a skin tissue damage temperature threshold. Temperatures below the threshold produce no significant damage. The threshold depends on time and temperature. For periods of time (for example, between a few milliseconds and about one second) the damage to blood and blood vessels, the damage threshold is about 44°. For shorter laser pulses, such as a few microseconds, the threshold is somewhat higher in the range of about 66° to 72° C.

If the laser pulse is very short (typically between several nanoseconds [$10^{-9}$ seconds] to one microsecond [$10^{-6}$ seconds]) the tissue may be damaged due to explosion or evaporation in the area of laser absorption. The laser energy is absorbed by skin tissue, however laser pulse duration is very short and there is not enough time for the tissue to expand or for the heat to spread out of the laser spot. In these conditions the tissue is mechanically ruptured in the region of laser absorption.

Thermal Vs. Ablation and Disruption

Figure 9:
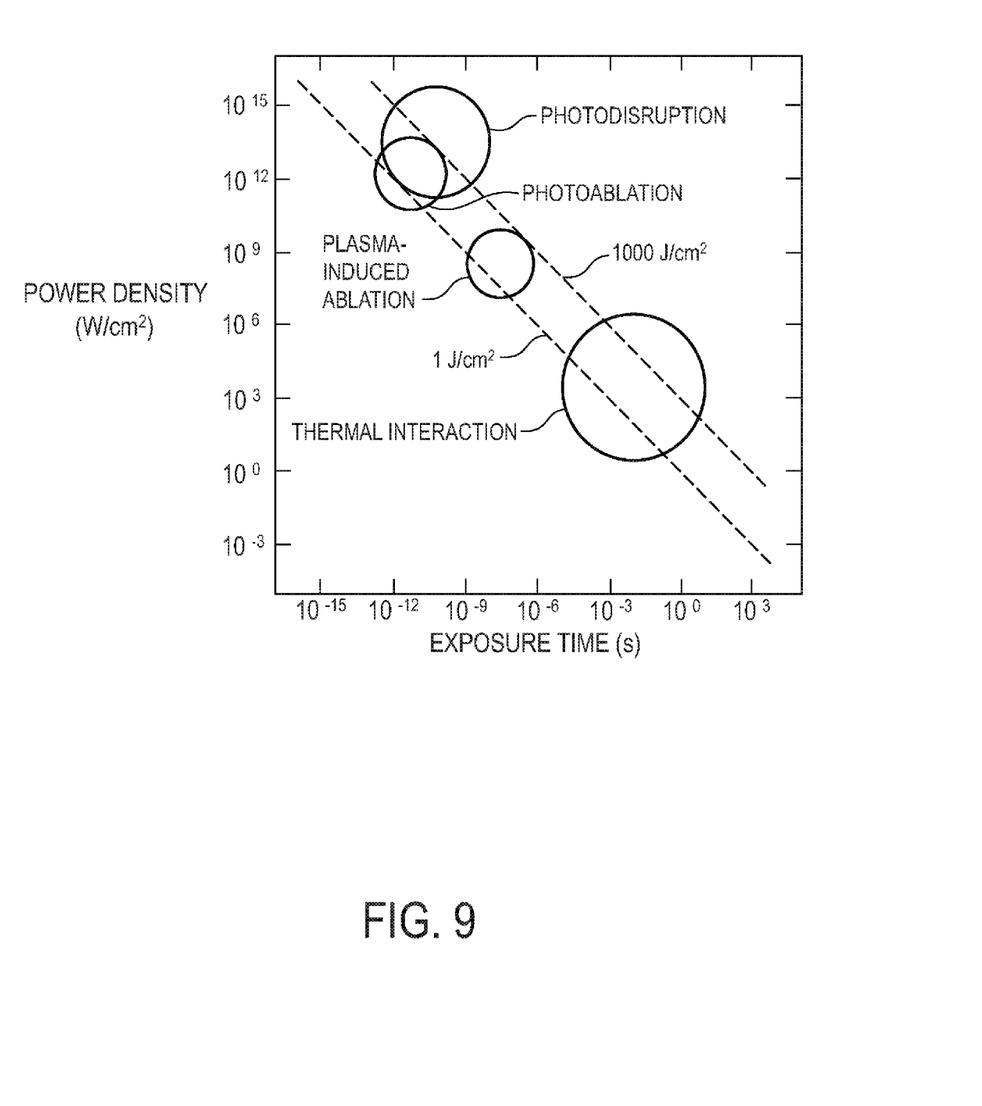
FIG. 9 is a map of laser-tissue interactions.

FIG. 9 is a chart showing the types of laser tissue interactions as a function of power density and exposure time. For pulse durations longer than about 1 microsecond the laser-tissue interactions are thermal. For pulses shorter than 1 microsecond the effects tend to be mechanical in the form of ablation or tissue disruption.

Laser Drug Delivery

Laser at wavelengths of high absorption in skin are used to damage and remove some parts of the skin layers. After that a topical substance (such as gel, cream, etc.) could be applied to the damage area. A better penetration rate of this substance into the body is observed in this case. This principle is used for laser drug delivery.

The Need

What is needed is a low cost laser system or laser handpiece to produce precise damage in small regions of tissue and delivering a topical substance such as a filler which will penetrate into laser damage regions at the same time or after the laser treatment.

SUMMARY OF THE INVENTION

The present invention provides a laser system and laser handpiece and process for skin treatment. The system includes (1) components for producing a continuous or pulse laser beam, and (2) components for delivering a substance to the damaged region of skin. The system is designed to control and utilize the laser beam for damaging a small volume of skin tissue and using a disposable tip to deliver a substance which is applied simultaneously or with some delay producing a combination of laser action with the action of a named substance at the same time. In preferred embodiments a laser beam is delivered to produce on the skin a single damage or multiple damages using a scanning system or optical system to produce a plurality of laser beams. The topical substance delivery tip can have one or multiple applicators with one or multiple substances delivered from individual applicators.

The topical substance can be a medication, skin care product, cosmetic, or dye for example.

The topical delivery tip can also be used with a skin electroporation system for delivering topical substances when skin is damaged by electric energy.

The system also includes a laser handpiece designed to deliver skin surface cooling. In preferred embodiments, the surface cooling is provided with a flow of cold air. The cold air in preferred embodiments is at a temperature of about 0 to 3° C. and may be provided with a commercial off-the-shelf cooling air unit or with a simpler unit consisting of a blower unit, an accumulator and a tube coiled in an ice water bath.

The topical delivery tip can be combined with any other laser handpiece of existing dermatological and cosmetic lasers.

DETAILED DESCRIPTION OF PREFERRED EMBODIMENTS

Preferred Embodiments

Figure 1:
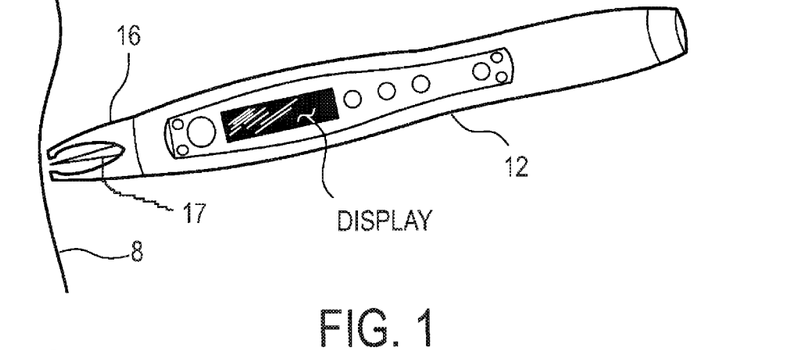
FIG. 1 is a drawing of a preferred embodiment of the present invention.
Figure 2:
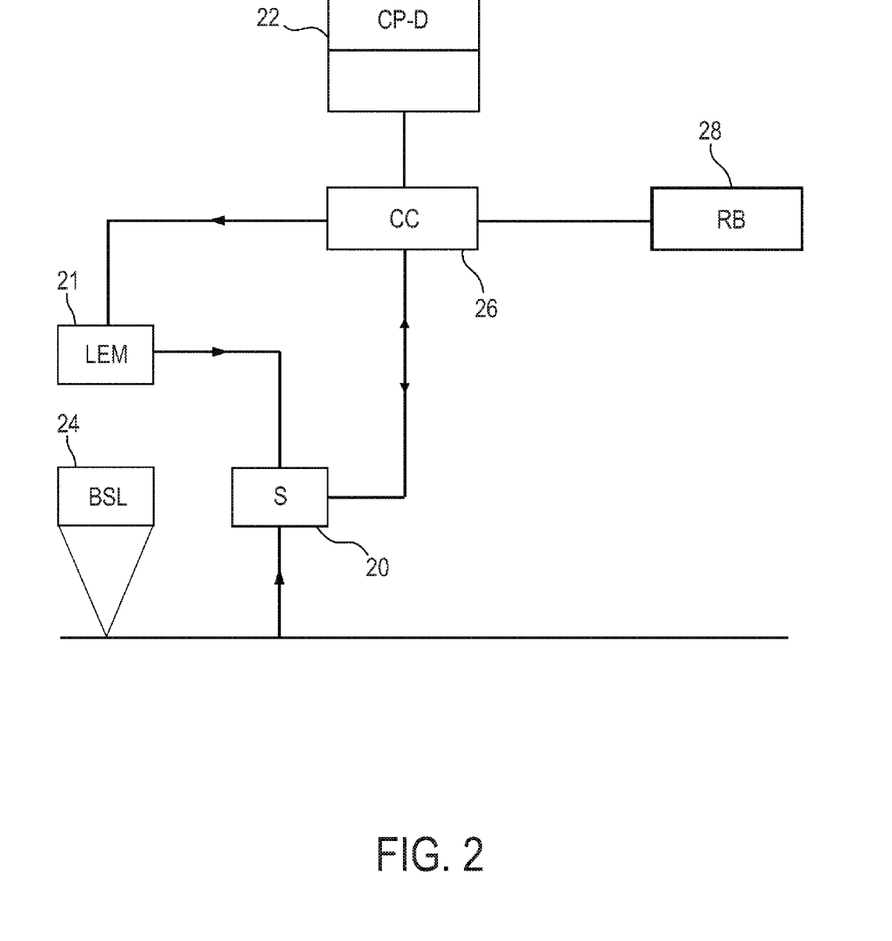
FIG. 2 shows a block diagram of the handheld battery operated laser handpiece.
Figure 3:
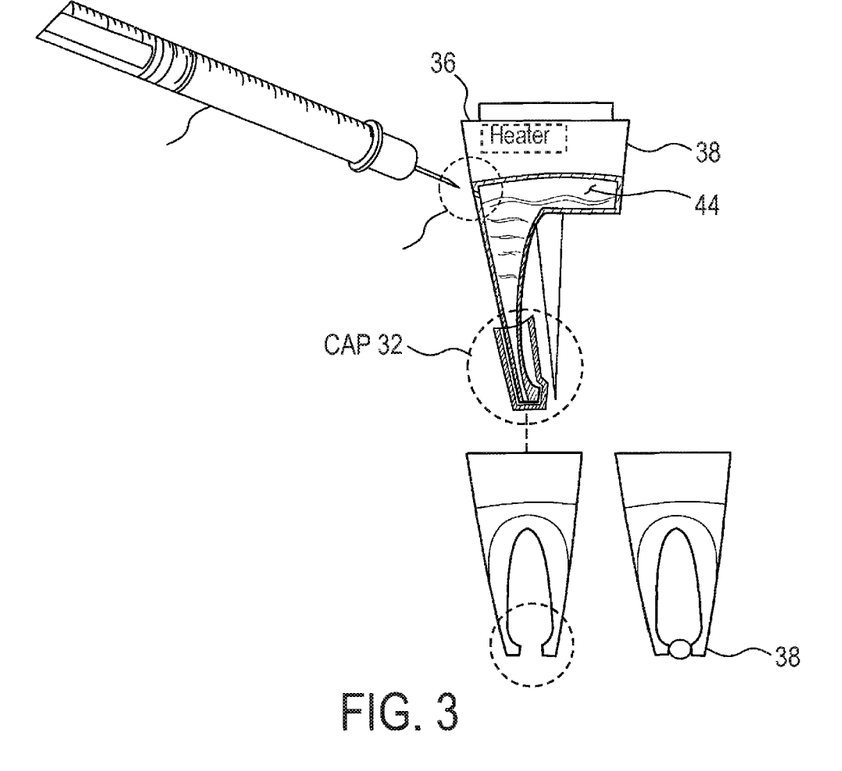
FIG. 3 shows a detailed design of the topical delivery tip.

FIGS. 1 through 3 show features of preferred embodiments of the present invention. A preferred embodiment is related to lip augmentation and wrinkle filling by laser filling with Hyaluronic acid. As shown in FIG. 1 the embodiment includes laser handpiece 12, a replaceable disposable tip 16 which is a standoff for optimal focusing of the laser beam 17 and simultaneously is an applicator of different fluid, cream, or gel type substances on the surface of the skin 8. In the preferred embodiment the laser is a handheld battery operated laser. FIG. 2 shows the block diagram of the laser handpiece. It consists of light emitting module 21 with beam shaping lenses 24, control circuit 26, re-chargeable battery 28, sensors 20 and a control panel with a display 22. In the preferred embodiment the light source is a laser diode. The wavelength of the laser diode is 1930 nm. The laser output is laser pulses, the energy of pulses and its repetition rate is set at the control panel and displayed at the screen. The laser beam is focused by the beam shaping lenses in a small spot at a distance of the length of the tip standoff 23.

The detailed design of the disposable tip is shown at FIG. 3. The tip is made of a translucent medical grade plastics and is kept in a sterilized individual bag. The internal volume 44 of the tip 38 is filled with a fluid, cream or gel substance. Before use the cap 32 on the top of the tip is removed and the tip is snapped to the laser. During the treatment the tip is sliding on the skin, the substance from the tip is applied onto the surface of the skin though a small opening made after removing the cap due to capillary effect. FIG. 3 shows that the substance can be applied also via mini ball applicator 38. In this preferred embodiment the fluid is hyaluronic acid. The fluid in the tip could be slightly heated up with electrical heater 36 or by energy split from laser light.

Application of the fluid takes place after the laser damages the skin. In the preferred embodiment with specific wavelength 1930 nm the laser pulses make a small opening in the stratum corneum, hyaluronic acid penetrates into the opening as a filler (http://en.wikipedia.org/wiki/Hyaluronan#Cosmetic_applications). Thus the described device is a compact-handheld non-expensive, easy to use system that combines all in one laser delivery device and a delivering substance.

Other Preferred Embodiments

Figure 4:
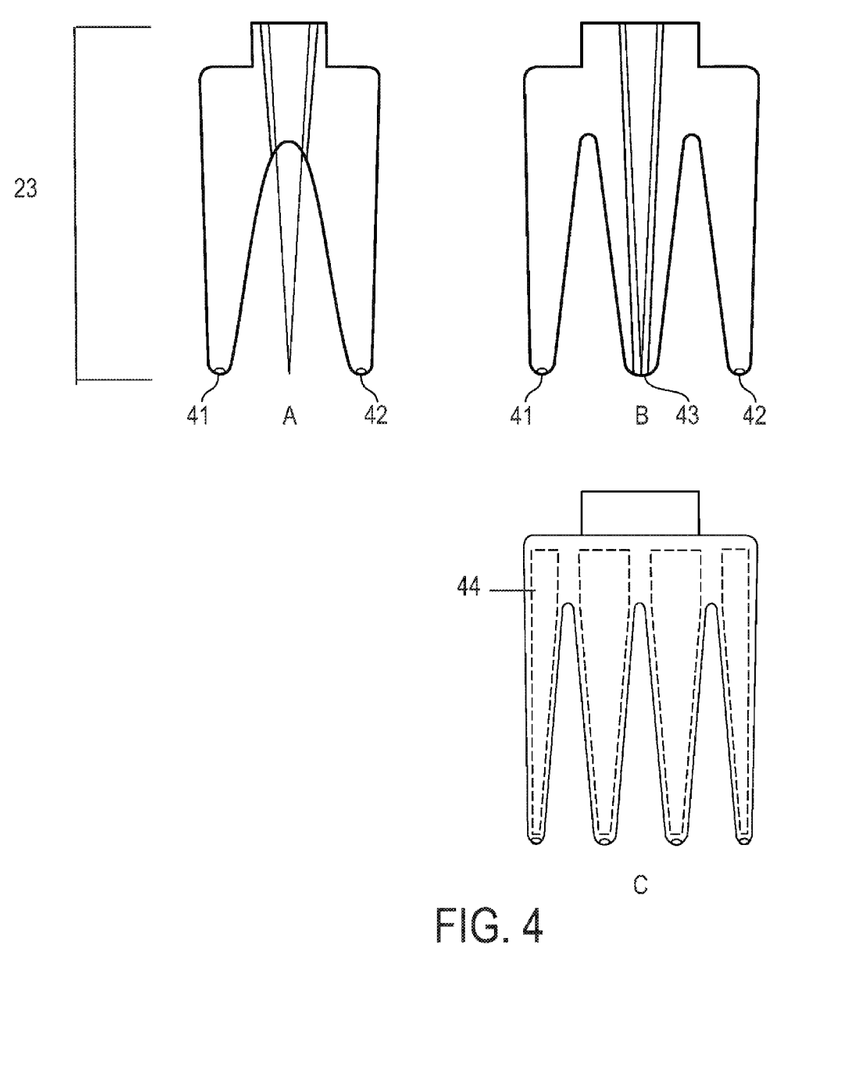
FIG. 4A through 4C show topical delivery tips with two and more applicators.

The tip can consist of more than one standoff as shown at FIG. 4a, 4b, and 4c. Each one can contain different substances which can be applied right before, after and during laser action. For example for a dual standoff tip the first substance can be an anesthetic which is applied before laser action (at opening 41) and the second substance can be a therapeutic or skin care substance for skin treatment which is applied after laser damage. FIG. 4b shows the tip with three substances which are applied before (at opening 41), during (at opening 43), and after (at opening 42) laser action. FIG. 4c shows the delivery tip with multiple applicators.

Figure 5:
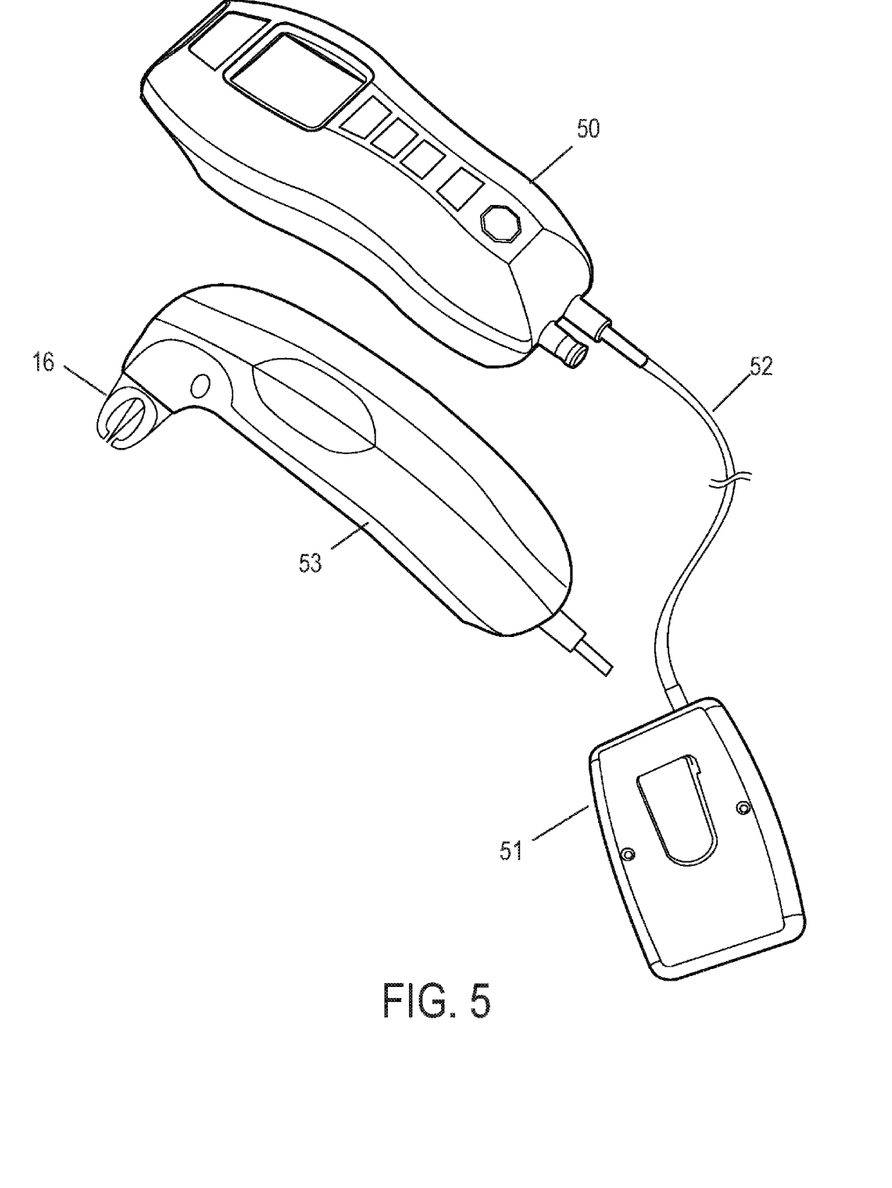
FIG. 5 shows a handheld battery operated laser with an internal scanner and topical delivery tip.

The disposable tip can be used with other handheld lasers. FIG. 5 shows a handheld laser 53 with a scanner 50. The laser produces a line of laser damages on skin, has a more powerful laser module and can be used for treatment of large areas of skin. To provide a source of energy to that more powerful laser a re-chargeable battery 51 is attached to the laser by cable 52. The battery 51 can be clipped to the waist belt or be carried in a pocket. This system is also designed to deliver skin surface cooling. In preferred embodiments the surface cooling is provided with a flow of cold air. The cold air in preferred embodiments is at a temperature of about 0 to 3° C. and may be provided with a commercial off-the-shelf cooling air unit or with a simpler unit consisting of a blower unit, an accumulator and a tube coiled in an ice water bath.

The disposable tip can be adopted to be attached to the handpieces of other stationary medical and cosmetic lasers which are commercially available or already being used in practice.

The disposable tip can be used with a skin electroporation system. In this case damage to skin is produced by electrical energy and not light as in the case of lasers.

Hand Piece

Figure 6:
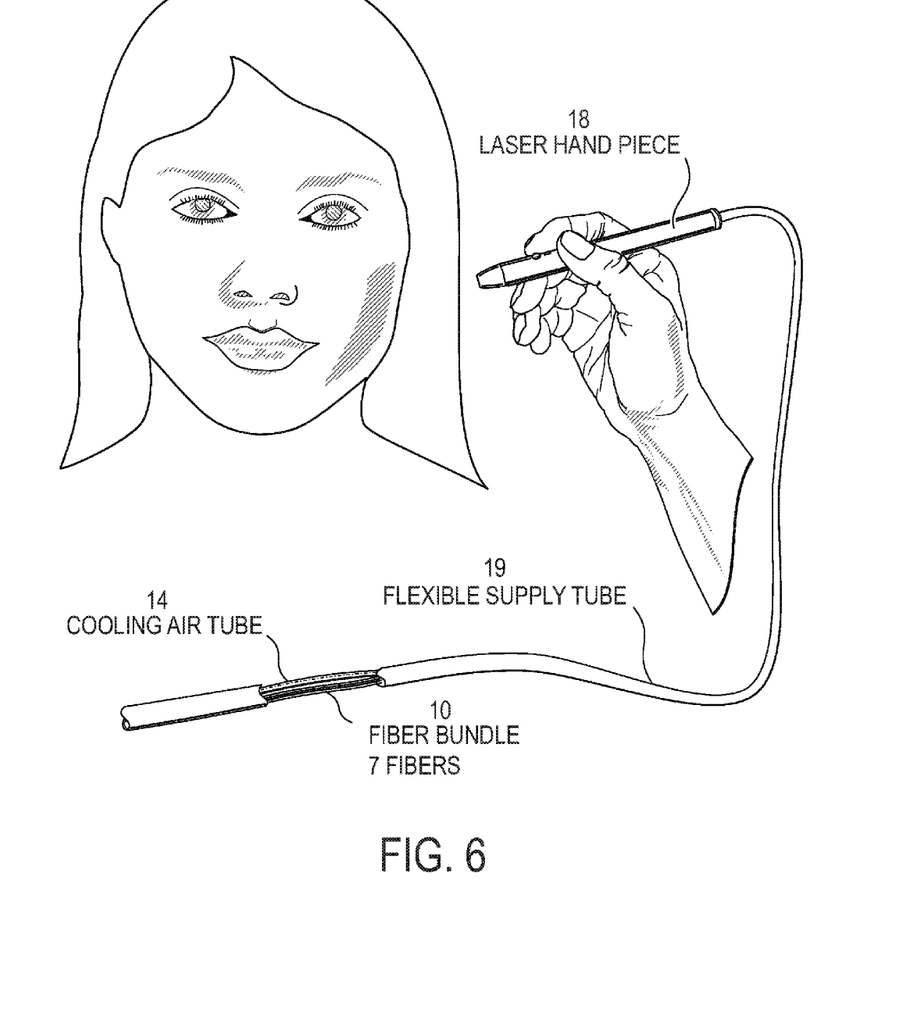
FIG. 6 shows the handpiece being applied to a patient.

FIG. 6. shows the system in operation with a handpiece being used to treat the face of a patient, the system comprising remote handpiece 18, flexible supply tube 19, cooling air tube 14, fibers 7, and fiber bundle 10. In this embodiment a focused laser beam damages tiny volumes of skin tissue about 0.05×0.1 mm at the surface of the skin. Due to the compact size of the device the procedure can be performed by a medical practitioner (doctor, nurse, etc) or by the patient himself. The laser handpiece can have an internal scanner to provide multiple laser damage at one position of the handpiece, also the beam shaping lenses can be designed in such a way to provide application of plurality of laser beams.

Other Applications of the Present Invention

The above embodiments describe techniques for skin treatments based on the concept of a combination of a laser delivery system and topical substance applicator both in one handpiece. The laser beam produces damage and the applicator delivers the substance from the tip to the damage zone. That combination provides a convenient way to deliver a filler or other medical, cosmetic or skin care substance under the surface of the skin thus improving the skin appearance. This concept can be extended to other types of treatments. Some of these other types of treatments are discussed below:

Large Area Skin Treatment

A handheld laser with scanning system is used for large area skin treatment. For skin rejuvenation purposes tips with vitamins and antioxidants in fluid form, stem cell factors, could be used. This combination is for large area skin rejuvenation including neo-collagen formation, sebaceous gland and bulge area stem cell mobilization.

Laser Assisted Anti-Aging Process for Skin

The laser beam is made by 1930 nm laser diode pulses, these laser pulses are used to perforate the stratum corneum. Then an active topical agent (cream, gel, suspension, solution, etc) with vitamins, antioxidants, stem cell factors is applied. The active ingredients of the topical agents penetrate into the skin via micro openings and get into the tissue. This treatment can be combined with a second wavelength at 1550 nm which penetrates deeper into the skin and provides additional heating to increase the speed and efficacy of action of the topical substance. Due to elevated temperature of the tissue the absorption and activity of the active ingredient increases and enhances the overall efficiency of the skin anti-aging procedure.

Treatment of Acne and Acne Scar Tissue

The short laser pulses of 1930 μm rupture the upper surfaces of a scar making the scar tissue safer, and helps such surface rejuvenation. This combination can also be used for skin rejuvenation.

Hair Treatment (Removal and Regrowth)

Another efficient combination of the tip is its combination with a short Q-switched pulses of 1064 nm Nd:YAG laser. The hair removal process with that type of lasers is greatly enhanced if a special black ointment is applied prior to laser procedure. Usually the ointment application procedure is cumbersome because it is soiled when applied by hands. The use of a tip filled with the black ointment and its application before lasing would make this procedure much easier and cleaner.

The wavelength of 1930 nm from preferred the embodiment or around 2900 nm (2790 nm, 2940 nm) or around 10600 nm can be used to produce small openings in the skin on the skull. The tip filled with stem cells, stem cell growth factors and/or medications applied through the tip applicator right after laser pulses will produce treatment to stimulate hair re-growth.

Treatment of Rhytides, Scars and Wrinkles

Applicants recommend a combination of 980 nm and 1440 nm and 1930 nm for treatment of rhytides, scars and wrinkles. The 980 nm beam is used to produce deep penetration of laser energy into the tissue, the 1440 nm is used to access subcutaneous collagen and 1930 nm beams is used to produce rupture of the stratum corneum and create an opening in the skin. These laser wavelengths can be combined with a disposable tip filled with hyaluronic acid, botox, fibroblasts, and other fillers, as well as with stem cell factors and other therapeutics.

Treatment of Telangiatesia and Pigmented Lesions

Applicants recommend 980 nm and 532 nm or 540 nm for telangiatesia and pigmented lesions treatments. The 980 nm is for deeper penetration into the tissue and 532 nm or 540 nm are for shallow penetration. Wavelengths in the range of 980 nm provide uniform preheating of and around the vessels and blood plasma. The small blood vessels are then destroyed by the energy of extremely short pulses of 532 nm or 540 nm laser beams which are strongly absorbed as shown in FIGS. 7 and 8. This treatment will be efficient with anti-angiogenic treatment delivering a drug (like avastin or lucentis) or an anti-angiogenic antibody provided with the use of the tip with those substances. This will inhibit re-appearance of destroyed blood vessels.

Pigmented Lesions

For treatment of pigmented lesions and wrinkles Applicants recommend a combination of 980 nm, 532 nm and 1440. The 980 nm beam is to form an energy cavity with deep penetration (several mm) and 532 nm and/or 1440 nm are used to form energy drops to treat pigmented lesions and wrinkles at the same time as described above.

Collagen Modification

Some skin treatment procedures like for example subcutaneous injection of live fibroblasts specifically target collagen fiber modifications. Combination of the delivery of that and similar substances with the help of a delivery tip and a laser have double folded benefits. First the laser produces an opening in the skin and provides a delivery pathway for the active substance that modifies collagen fibers and structure, also laser damage of the skin and collagen fibers induces an endogenous process of collagen modification. Those two processes acting together significantly increase the efficacy of collagen modification and lead to skin rejuvenation.

Temporal Tattoo for Medical and Aesthetic Purposes

The tip can be filled with a dye. After the rupture of the stratum corneum by the laser the dye from the tip applicator penetrates into micro-holes in the upper layer of skin and can stay there for some time producing a tattoo. Since the depth of the skin opening is very superficial compared to traditional tattoo needles, the tattoo does not stay long, thus this process can be used as a temporal tattoo for aesthetic and therapeutic purposes.

Laser Suppliers

The handheld lasers systems with single or dual wavelength with or without a scanner can be obtained from Dolleris Technology with offices in Vancouver, Canada and Intezity Innovation (Hvidovre, Denmark).

All of the above combinations of wavelengths can be obtained by using powerful laser diodes. The laser diodes can be obtained from a number of manufacturers like nLight, with offices in Vancouver, Canada; Coherent, with offices in Santa Clara, Calif. and IPG Photonics, with offices in Oxford, Mass.

Other laser suppliers include Palomar (Burlington, Mass.), Cynosure (Westford, Mass.), Candela (Wayland, Mass.), Sciton (Palo Alto, Calif.), Lumenis (Santa Clara, Calif.), Cutera (Brisbane, Calif.), Lutronic (Fremont, Calif.).

The reader should understand that the above specific embodiments of the present invention are merely examples and that many changes and modifications could be made without departing from the important concepts of the present invention. For example, many sources of radiation at different wavelengths that are scattered and absorbed in tissue and skin with specific configuration and time relationship may be substituted for the lasers described in detail. In fact the above-described source of radiation could be any source of electromagnetic energy that meets the above-described criteria, such as microwave, radio frequency, light (laser diodes, light emitting diodes (LED), non-coherent light source), etc. Those sources of radiation are to be combined with a disposable tip that delivers a topical substance onto the surface of skin before after or during the action of the radiation.

We claim:

1. A laser device for simultaneously delivering a therapeutic composition and laser energy to the skin of a subject, the device comprising:
   a) a laser handpiece comprising a laser diode; and
   b) a disposable tip for delivering at least one therapeutic composition to the skin of the subject, wherein the disposable tip has a top and a bottom, and wherein the disposable tip (i) is configured to detachably connect to the laser handpiece at the top of the disposable tip, and (ii) comprises a plurality of applicators, each applicator comprising a reservoir for containing the at least one therapeutic composition, wherein each applicator comprises an opening for placing the reservoir in fluid communication with the skin of the subject, wherein the openings are configured to contact the skin of the subject, wherein the bottom of the disposable tip terminates in the plurality of applicators, and wherein the disposable tip is in contact with a removable cap that covers the openings in the applicators.

2. The device of claim 1, wherein the laser diode is configured to deliver a continuous or pulse laser beam.

3. The device of claim 1, wherein each reservoir contains at least one of a medication, skin care product, anesthetic, vitamin, antioxidant, stem cell factor, stem cell, ointment, growth factor, dye, fibroblast, botox, hyaluronic acid, and a cosmetic.

4. The device of claim 1, wherein each reservoir contains a therapeutic composition that is in the form of a fluid, cream or gel.

5. The device of claim 1, wherein the openings are in fluid communication with a ball applicator that is configured to apply the at least one therapeutic composition onto the skin of the subject.

6. The device of claim 1, wherein the laser diode emits laser energy at a wavelength of 532 nM, 540 nM, 980 nM, 1.064 nM, 1,440 nM, 1,550 nM, 1,930 nM, 2,790 nM, 2,940 nM or 10,600 nM.

7. The device of claim 1, wherein the disposable tip comprises a heater for heating the at least one therapeutic composition.

8. The device of claim 1, wherein the device comprises an air cooling unit configured to cool the skin of the subject.

9. A device for simultaneously applying a therapeutic composition and laser energy to the skin of a subject, the device comprising:
   a) a handpiece comprising a laser diode; and
   b) a disposable tip, wherein the disposable tip is configured to detachably connect to the laser handpiece, and wherein the disposable tip comprises (i) a plurality of applicators each comprising a reservoir for containing at least one therapeutic composition, (ii) an opening in each applicator that is configured to contact the skin of the subject and place each of the applicators in fluid communication with the skin of the subject, and (iii) a removable cap for preventing the at least one therapeutic composition from escaping through the opening in each reservoir;
   c) wherein the disposable tip terminates in the plurality of applicators.

10. The device of claim 9, wherein each reservoir contains at least one of a medication, skin care product, anesthetic, vitamin, antioxidant, stem cell factor, stem cell, ointment, growth factor, dye, fibroblast, botox, hyaluronic acid, and a cosmetic.

11. The device of claim 9, wherein the disposable tip comprises a ball applicator that is (i) in fluid communication with the opening in each applicator, and (ii) configured to apply the at least one therapeutic composition onto the skin of the subject.

12. The device of claim 9, wherein the laser diode emits laser energy at a wavelength of 532 nM, 540 nM, 980 nM, 1,064 nM, 1,440 nM, 1,550 nM, 1.930 nM, 2,790 nM, 2,940 nM or 10,600 nM.

13. The device of claim 9, wherein the disposable tip comprises a heater for heating the at least one therapeutic composition.

14. The device of claim 9, wherein the device comprises an air cooling unit configured to cool the skin of the subject.

15. A device for simultaneously applying a therapeutic composition and laser energy to the skin of a subject, the device comprising:
   a) a laser handpiece comprising a laser diode that emits laser energy at a wavelength of 532 nM, 540 nM, 980 nM, 1,064 nM, 1,440 nM, 1,550 nM, 1,930 nM, 2,790 nM, 2,940 nM or 10,600 nM; and
   b) a disposable tip wherein the disposable tip is configured to detachably connect to the laser handpiece;
   c) wherein the disposable tip comprises a plurality of applicators, each comprising (i) a reservoir for containing a therapeutic composition, and (ii) an opening for placing the reservoir in fluid communication with the skin of the subject, wherein the opening is configured to contact the skin of the subject;
   d) wherein the disposable tip terminates in the plurality of applicators;
   e) wherein the laser handpiece comprises beam shaping lenses that focus laser energy from the laser diode at a distance that corresponds to the length of the applicators; and
   f) wherein the beam shaping lenses focus laser energy on the surface of the skin of the subject when the applicators are in contact with the skin of the subject; and
   g) wherein the disposable tip is in contact with a removable cap that covers the openings in the applicators.

16. The device of claim 1, wherein the laser handpiece comprises beam shaping lenses that focus laser energy from the laser diode at a distance that corresponds to the length of the applicators.

17. The device of claim 1, wherein the laser handpiece comprises beam shaping lenses that focus laser energy on the surface of the skin of the subject when the applicators are in contact with the skin of the subject.

18. The device of claim 9, wherein the laser handpiece comprises beam shaping lenses that focus laser energy from the laser diode at a distance that corresponds to the length of the applicators.

19. The device of claim 9, wherein the laser handpiece comprises beam shaping lenses that focus laser energy on the surface of the skin of the subject when the applicators are in contact with the skin of the subject.

* * * * *